United States Patent [19]

Welander

[11] Patent Number: 4,507,798
[45] Date of Patent: Mar. 26, 1985

[54] DEVICE FOR PERFORMING X-RAY EXAMINATIONS OF THE TEETH

[76] Inventor: Ulf E. S. Welander, Sofiehemsu 16, 90239, Umeå, Sweden

[21] Appl. No.: 434,628

[22] Filed: Oct. 15, 1982

[30] Foreign Application Priority Data

Nov. 4, 1981 [SE] Sweden .................. 8106534

[51] Int. Cl.³ .............................. A61B 6/14
[52] U.S. Cl. ........................ 378/170; 378/168
[58] Field of Search .............. 378/168, 169, 170

[56] References Cited

U.S. PATENT DOCUMENTS

| | | | |
|---|---|---|---|
| 2,392,109 | 1/1946 | Vlock | 378/170 |
| 2,786,947 | 3/1957 | Lieberman | 378/168 |
| 2,899,559 | 8/1959 | Maurer . | |
| 3,003,062 | 10/1961 | Updegrave | 378/170 |
| 3,304,422 | 2/1967 | Medwedeff . | |
| 3,473,026 | 10/1969 | Updegrave . | |

FOREIGN PATENT DOCUMENTS 226679 6/1969 Sweden .

Primary Examiner—Alfred E. Smith
Assistant Examiner—T. N. Grigsby
Attorney, Agent, or Firm—Finnegan, Henderson, Farabow, Garrett & Dunner

[57] ABSTRACT

A device for performing X-ray examinations of the teeth comprises a film holder which is detachably connectable to an arm which in turn is detachably connectable with an aligning disc. An opening in the aligning disc is provided to position the X-ray machine when the device is assembled in alignment with the X-ray film. The arm, the aligning disc and the film holder are so designed that exposure can take place with lying as well as standing film, that the upper as well as the lower gum can be exposed, and that the arm may be connected to the left as well as to the right. The invention also includes an extension part by means of which the biting surface may be increased.

8 Claims, 11 Drawing Figures

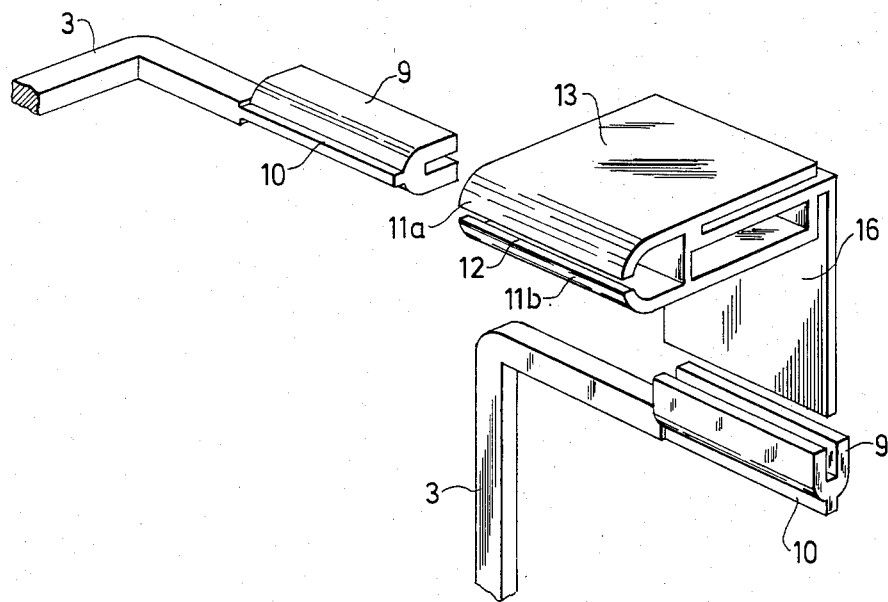
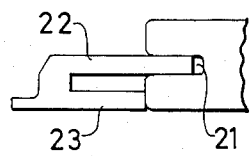
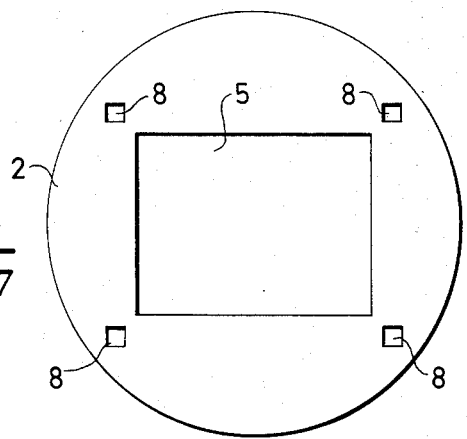

4,507,798

DEVICE FOR PERFORMING X-RAY EXAMINATIONS OF THE TEETH

BACKGROUND OF THE INVENTION

The present invention relates to a device for performing dental X-ray examinations.

It is of great importance that dental X-ray examinations may be performed in a safe and comfortable way for the patient and that all kinds of examinations may be performed rapidly using one single equipment.

It is previously known to use specially designed film holders to securely hold the film during the actual exposure. The requirements upon such film holders may be summarized as follows:

The film holder should be hygienic, i.e. either of the disposable type or possible to sterilize and in all cases it must be able to be disinfected. It must last all the exposures required for one patient during one examination occasion.

It should be possible to use it in most or preferably all existing situations, by exposure of periapical pictures as well as by exposure of bite-wing pictures and it should be possible to use it by up-right as well as resting film location. By exposure of periapical pictures it must be so thick that it permits the edge of the film to be placed above the occlusion plane.

By exposure of bite-wing pictures it must be so thin that the teeth in the upper and lower gums need not be unnecessarily kept apart.

It must be provided with such a long biting plate that a stable biting of the teeth is obtained in such cases where the film is located relatively far away from the teeth, e.g. using a so called parallel technique when examining the teeth of the upper gum or the front of the lower gum.

It must have so short a biting plate that it does not interfere for example by engaging the cheeks when examining the side portions of the lower gum.

It must be easy to handle and uncomplicated to use by dentist or nurse.

It should be comfortable to the patient but should at the same time offer a stable biting that secures the film in a definite position.

It should support the film and prevent it from bending. It must not generate interfering shadows by high absorption of X-rays.

It is a further desire that dental X-ray examinations could be performed rapidly and efficiently so that for example the need for repeating is minimized.

The film holders hitherto developed have only partiallay fulfilled the requirements and wishes disclosed above.

The object of the invention is therefore to provide an device fulfilling the abovementioned requirements and wishes and which furthermore may be produced at a low cost.

To accomplish these and other objects the invention has the characteristics disclosed in the following description and claims.

In the accompanying drawings an exemplifying embodiment of the invention is shown as well as a modification thereof.

BRIEF DESCRIPTION OF THE DRAWINGS

FIG. 4 is a perspective view of the connection between the film holder and the guiding arm:

FIG. 5 shows a somewhat modified connection between the film holder and the guiding arm:

FIG. 6 shows a shielding-off disc connectable to the guiding arm:

FIG. 1 shows in principle how a dental X-ray examination according to the invention may be performed.

DESCRIPTION OF THE PREFERRED EMBODIMENTS

Figure 1:
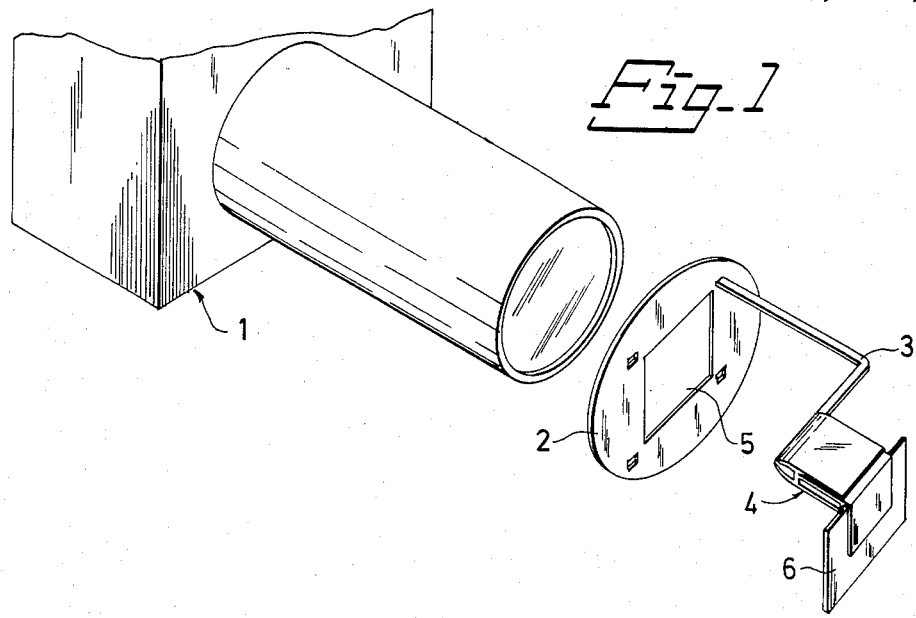
FIG. 1 is a perspective view of the schematic structure of a device according to the invention.

Reference numeral 1 thereby designates an X-ray machine of conventional type. As is known, such a machine is universally adjustable so that the picture frame thereof may be brought into register with the film positioned in the film holder to be exposed.

Numeral 2 denotes a shielding-off disc connected to a film holder 4 by means of an arm 3. The connection between the disc 2 and the film holder 4 is so designed that an exposure opening 5 in the disc always will be located in register with a film 6 inserted into the film holder and it is easily understood that the adjustment of the X-ray machine is considerably facilitated as the dentist or the nurse only has to center the machine in relation to the disc 2 and by means of the length of the arm 3 said disc will always be located in the immediate vicinity of the cylindrical end portion of the X-ray machine. Consequently, it is the patient herself that secures the guiding means defined by the shielding-off disc 2 into the correct position.

Figure 3:
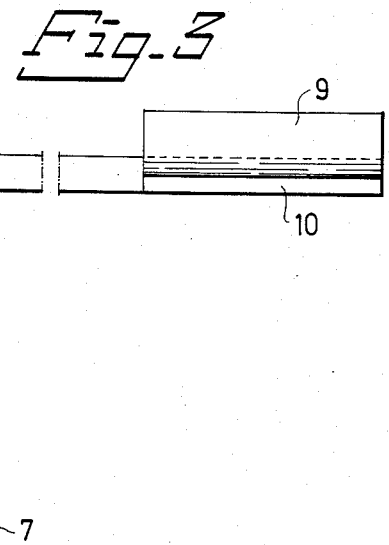
FIG. 3 is a guiding arm forming part of the device.

In order to permit such adjustment in upright and resting film positions respectively and by the examinations which will be further discussed below the disc 2 and the arm 3 are designed to be connected to each other in a number of different ways. For this purpose the arm 3 has, as may be seen in FIG. 3, a conically shaped connecting part 7, square in section. Further, according to FIG. 6 the disc 2 has a number, four in the illustrated embodiment, of openings 8, which are square and conically shaped so that the connecting part 7 of the arm 3 by insertion into each opening 8 respectively, may be brought to connect the arm to the disc by means of frictional force. Naturally, this frictional connection may be replaced by a snap device or some other type of rapidly releasable connection means. It is understood that by this arrangement the arm may be fixed in a number of locations in relation to the disc.

Figure 2:
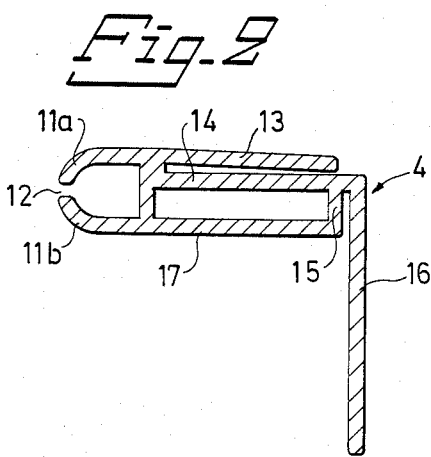
FIG. 2 is a section through a film holder forming part of the device.

In order to permit connection of the arm 3 to the film holder 4 with the latter in two alternative positions, the arm according to FIG. 4 in the end opposite to the connecting part 7 has a second connecting part which in the embodiment shown in FIG. 4 has a portion 9 with U-shaped section from the web portion of which projects a portion 10 parallel to the legs of the U-shaped portion 9. Since according to FIG. 2 and 4 the film holder has a design of the sockets 11a, 11b, 12a matching the portions 9, 10, it is understood that the arm 3 may be connected to the film holder 4 by sideways pushing the portions 9, 10 of the arm into said socket means in the film holder. As may be seen in FIG. 2 the film holder 4 has two walls 13, 14 between which an X-ray film may be applicated and two walls 15, 16 perpendicular thereto and an X-ray film may be positioned between these. By selecting the thickness of the wall 16 in such a manner that it substantially corresponds to the distance between the U-shaped legs of the portion 9 it is understood that the arm 3 may also be connected to the thin wall 16 of the film holder 4 in a manner indicated in the lower right hand side of FIG. 4.

Figure 7:
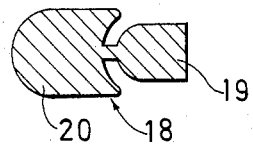
FIG. 7 is a section through a film holder extension.

For some examinations a longer biting surface is required than the one offered by the walls 13 and 17 and for this purpose an extension part 18 according to FIG. 7 may be used. This extension part has a portion 19 that fits into the socket 11a, 11b, 12 and a portion 20 constituting the actual extension.

Figure 10:
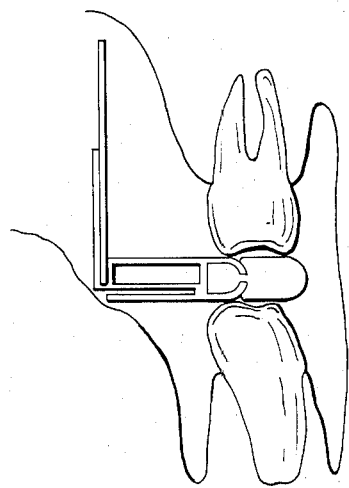
FIG. 10 shows the principle for the exposure of the molar region of the upper gum.
Figure 11:
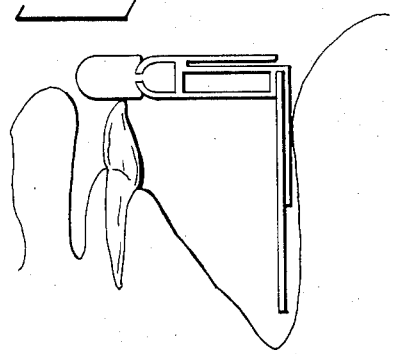
FIG. 11 shows the principle for the exposure of the lower gum front.

In FIGS. 10 and 11 examples of examinations are shown in which an extension part according to FIG. 7 is well suited.

Figure 8:
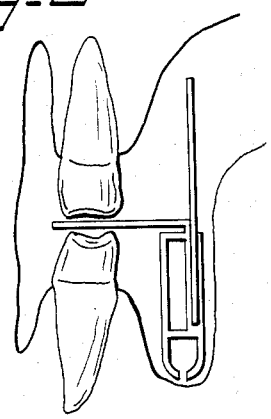
FIG. 8 shows the principle for a so called bite-wing exposure.
Figure 9:
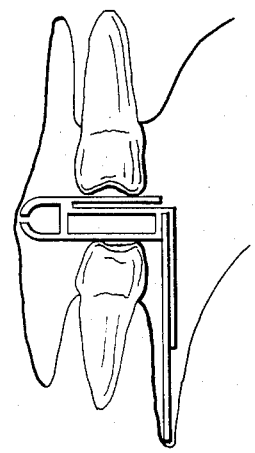
FIG. 9 shows the principle for a premolar picture in the lower gum.

FIG. 8 shows the exposure of a bite-wing picture and as may be seen, the biting in this case is performed engaging the thin part 16 of the film holder. In the examination according to FIG. 9 the biting rather takes place engaging the thicker portion of the film holder and the film is resting. Also by the examination according to FIG. 10 resting film is used and as mentioned, an extension part is used. Finally, in examination according to FIG. 11 an extension part is used and the film is placed in an upright position.

As may be seen from the discussion above, the improved aid according to the invention offers dental X-ray examinations of the most varying types by using a few very simple and easy-to-handle elements at the same time as the adjustment of the X-ray machine is considerably facilitated and hereby the risk for e.g. incorrect adjustment etc. resulting in repeated exposures is drastically reduced.

In the modification of the connecting portion shown in FIG. 5 the film holder has a slot 21 in the thicker portion thereof and the connecting portion of the arm is defined by two projecting walls 22, 23 one of which 22 is longer that than the other. The distance between the walls 22, 23 is so selected that it corresponds to the wall thickness of the thinner wall 16 of the film holder in order that a frictional grip may obtained in the two connection cases.

What is claimed is:

1. A device for performing dental X-ray examinations, comprising: a film holder substantially L-shaped in section and having a narrower portion and a thicker portion, said film holder being adapted to receive X-ray film in two alternative planes relative to the film holder and including a socket in the thicker portion; shielding-off means having a first connecting portion configured complementary to said socket and designed to be connected to said socket; and extension means having a second connecting portion configured complementary to said socket and designed to be connected to said socket, whereby either or both of said shielding-off means and said extension means are connected to said film holder.

2. A device according to claim 1, wherein said shielding-off means comprises means for adjusting and positioning the film holder in relation to an X-ray source.

3. A device according to claim 2, wherein said shielding-off means comprises an arm having a first end connected to said first connecting portion and a second end including a connecting part; and a disc adapted to receive said connecting part and having an exposure opening corresponding to an image field, said exposure opening being so positioned in relation to the connecting part that said exposure opening will register with the film to be exposed and held in the film holder.

4. A device according to claim 3, wherein said connecting part is square in cross section and conical, and said disc has a plurality of conical and square openings configured complementary to said connecting part of the arm and so positioned that the exposure opening will register with the film independently of the film being in a resting or upright position or occupying a right hand side or a left hand side position, upwardly or downwardly.

5. A device according to claim 1, wherein said extension means includes an extension portion defining an extension of the thicker portion of the film holder.

6. A device according to claim 1, wherein said socket in the thicker portion of the film holder includes a connecting slot, and wherein said first connecting portion includes a projecting wall of complementary thickness such that it fits into said connecting slot with a frictional grip and a shorter wall separated from said projecting wall by a distance substantially corresponding to the thickness of the narrower portion of the film holder.

7. A device according to claim 1, wherein said socket is of substantially dove-tail shape, and wherein said first connecting portion is of substantially dove-tail shape and includes a connecting recess in which the narrower portion of the film holder fits with a frictional grip.

8. A device according to claim 1, wherein said thicker portion includes a film slot to hold the X-ray film substantially parallel to said thicker portion and a film recess to hold the X-ray film substantially perpendicular to said thicker portion.

* * * * *